United States Patent
Miyazawa et al.

(10) Patent No.: US 6,869,911 B2
(45) Date of Patent: Mar. 22, 2005

(54) TILLERING PROMOTER FOR PLANT AND METHOD FOR TILLERING PROMOTION OF PLANT

(75) Inventors: Yuki Miyazawa, Kawasaki (JP); Masahiko Kurauchi, Kawasaki (JP); Hiroyuki Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/987,549

(22) Filed: Nov. 15, 2001

(65) Prior Publication Data

US 2002/0095695 A1 Jul. 18, 2002

(30) Foreign Application Priority Data

Nov. 27, 2000 (JP) ........................ 2000-358705

(51) Int. Cl.⁷ .................. A01N 43/36; A01N 43/90
(52) U.S. Cl. .................. 504/136; 504/287
(58) Field of Search ............... 504/136, 287, 504/118; 71/11, 27

(56) References Cited

U.S. PATENT DOCUMENTS

| 5,422,343 A | 6/1995 | Yamamoto et al. |
| 6,448,202 B1 * | 9/2002 | Miyazawa et al. .......... 504/136 |

FOREIGN PATENT DOCUMENTS

| EP | 0 841 007 | 5/1998 |
| EP | 1095565 | * 5/2001 |
| EP | 1 095 565 | 5/2001 |
| JP | 2852677 | 2/1999 |
| JP | 2001-131009 | 5/2001 |
| JP | 3515935 | 4/2004 |
| WO | 9110726 | * 7/1991 |
| WO | WO 91/10726 | 7/1991 |
| WO | WO 94/00009 | 1/1994 |
| WO | WO 91/00009 | 1/1997 |

OTHER PUBLICATIONS

Patent Abstracts of Japan, JP 2001–199812, Jul. 24, 2001.
Patent Abstracts of Japan, JP 63–045211, Feb. 26, 1988.
Patent Abstracts of Japan, JP 03–201914, Sep. 3, 1991.

* cited by examiner

*Primary Examiner*—Alton Pryor
(74) *Attorney, Agent, or Firm*—Oblon, Spivak, McClelland, Maier & Neustadt, P.C.

(57) ABSTRACT

Herein are disclosed a tillering promoter for a plant comprising an amino acid, especially proline, or inosine in addition thereto, as effective ingredient(s), and a method for tillering promotion for a plant wherein the tillering promoter is especially applied onto the leaf surfaces, in accordance with which are provided a tillering promoter for a plant which enables the reduction of the amount of fertilizer hitherto used in a large amount and the maintenance of a satisfactory green state by promoting the tillering of a plant, especially lawn grass without requiring the application of pesticides and plant hormones, also exhibits growth promotion and coloring promotion of leaves, is not a chemical fertilizer, and does not adversely affect the environment and men and beasts, and a method for applying the same.

11 Claims, No Drawings

US 6,869,911 B2

TILLERING PROMOTER FOR PLANT AND METHOD FOR TILLERING PROMOTION OF PLANT

BACKGROUND OF THE INVENTION

1. Technical Field Pertinent to the Invention

The present invention relates to a tillering promoter for a plant comprising, as the effective ingredient(s), an amino acid, especially at least one of arginine, glutamine and proline which is effective for increasing tillering (as well known, branching out from the joints of stems near to the roots of rice, barley and wheat, lawn grass or the like) and weight of living plant, or inosine in addition to the amino(s) acid, and to the use of such a tillering promoter for a plant, or it relates to a method for tillering promotion of a plant wherein the amino acid(s) and inosine are each applied to the same part(s) or different part(s) of the plant at the same time or at slightly different times (i.e., used in combination).

2. Related Art

The present inventors have previously developed a withering preventing and quick-acting nutrition supplementing agent for a gramineous plant comprising proline, one kind of amino acid, or inosine in addition thereto, as the effective ingredient(s) (Japanese Patent Application No. 308,281/1999). As a result of the studies for finding out further novel effects, the present inventors have achieved the present invention.

Hitherto, some examples have been known wherein an amino acid-related compound, e.g., proline is applied to a plant.

For example, (a) Japanese Patent Publication No. 42,566/1971 discloses a promoter of flower bud formation comprising at least one of uracil and cytosine, and proline.

However, since the increase of the number of tillering is not observed in the promoter of flower bud formation and the method of application is different from the case of the present invention, the promoter is obviously different from the present invention.

Furthermore, for the promotion of the tillering of lawn grass, there are known some examples wherein substances having indole skeleton(s) or plant hormone(s).

For example, (a) Japanese Patent Application Laid-open No. 267,803/1995 discloses a tillering promoter for a gramineous plant comprising an fluorine-containing indolebutyric acid derivative, e.g., an alkyl ester of 4,4,4-trifluoro-3-(indole-3-)butyric acid.

However, the tillering promoter is a chemical fertilizer and thus, it is obviously different from the present invention wherein amino acids, i.e., natural products are utilized, in view of the influence against the environment.

Moreover, (b) Japanese Patent Application Laid-Open No. 82,113/1995 discloses a growth promoter of lawn grass comprising a gibberellin and a cytokine.

However, the growth promoter for lawn grass comprises plant hormones of gibberellin and cytokine, and thus, there is a possibility of exerting undesirable influences on the natural environment, so that the promoter is obviously different from the present invention.

Furthermore, (c) Japanese Patent Application Laid-Open No. 201,914/1991 discloses a method for the promotion of the rooting and tillering of rice seedlings for transplantation, which comprises applying an amino acid fermentation liquid (containing, for example, proline, alanine, valine, and glutamic acid all together) during raising of seedlings in wet-rice farming.

However, in the method of tillering promotion, proline is not solely used, and the amount of the amino acid fermentation liquid to be used is defined as total concentration of the amino acids, so that these amino acids are placed on the same level, i.e., are treated as equivalents.

Incidentally, for example, lawns are utilized in many places such as parks, gardens and ball game fields, and are particularly indispensable for golf courses. However, a large quantity of fertilizers and pesticides has hitherto been used for maintenance of lawn grass and the use has become a big problem in view of the environmental aspect.

In particular, the stress by high temperature causes cold-district type lawn grass indirect growth stop and direct withering, but there is only a measure of good air-ventilation against the problems.

SUMMARY OF THE INVENTION

[Problems to be Solved by the Invention]

Thus, it is an object of the present invention to provide a tillering promoter for a plant which enables the reduction of the amount of fertilizer hitherto used in a large amount and the maintenance of a satisfactory green state by promoting the tillering of a plant, especially lawn grass without requiring the application of pesticides and plant hormones, also exhibits growth promotion and coloring promotion of leaves, is not a chemical fertilizer, and does not adversely affect the environment and men and beasts. Another object is to provide a method for applying the same.

[Means for Solving the Problems]

As a result of extensive studies for achieving the aforementioned objects, the present inventors have first found that an amino acid, especially proline exhibits a remarkable effect on the promotion of the tillering of lawn grass and inosine has an action of enhancing the tillering effect of the amino acid by promoting the growth of a plant. Accordingly, they have accomplished the present invention based on the findings.

Namely, the present invention relates to a tillering promoter for a plant comprising an amino acid, especially proline, or inosine in addition thereto, as effective ingredient(s), and a method for tillering promotion for a plant wherein the tillering promoter is especially applied onto the leaf surfaces.

DETAILED DESCRIPTION OF THE INVENTION

The following will explain the present invention in detail.

The target plants to which the tillering promoter of the present invention is to be applied include preferably lawn grass, but also rice, fruits vegetables, leafy vegetables, decorative plants, and the like.

As the amino acids, there may be mentioned arginine, glutamine and proline, and especially proline is effective, but these amino acids are not necessarily to be a purified one. They may be in the form of a protein hydrolysate or a mixture of amino acids containing a large quantity of proline unless it exerts an adverse effect. Each amino acid is preferably a product having a high purity of 90% or more (ratio of the amino acid per the total solute excluding the inosine in the tillering promoter for a plant of the present invention to be applied onto leaf surfaces).

The tillering promoter for a plant of the present invention comprising an amino acid, especially proline, as the effective ingredient can be prepared into a form wherein the effective ingredient is dissolved optionally in an appropriate solvent such as water or the like. Moreover, the promoter can be formulated into a powder, granules, or tablets by using an optional filler or binder. The application method is preferably foliar application. In this case, an amino acid concentration of 0.2 ppm to 0.2% (2,000 ppm), preferably 10 to 300 ppm, further preferably 100 to 300 ppm is effective. This is because no effect is exhibited at a concentration lower than the range, and there is a possibility of withering by excessive fertilization at a concentration higher than the range. By the way, in the case of dissolving in a solvent, it is optional to formulate the promoter by incorporating a fungicide, a surfactant, or a preservative in view of the prevention of rot. Furthermore, in the case of foliar application, the ombined use with a spreader is effective.

As the way of application of the tillering promoter including application timing, there may be mentioned application as an additional fertilizer, application after mowing grass, or the like. With regard to the way of fertilizing, it is particularly effective to apply amino acid(s), especially proline, to the above-ground part(s) such as foliar application or the like, and inosine to subterranean part(s) by spraying to soil, addition to hydroponic medium, or the like.

The foliar application of proline is effective not only for tillering promotion of a plant but also as a means for promoting the growth such as prevention of withering, feeding of fast-acting nitrogen, and the like. Moreover, the promotion of coloring leaves is also observed.

Application amounts of the tillering promoter for a plant of the present invention vary depending on the application timing, the kind of plants, cultivation density, growing stage, and so on. In short, the amounts may be ones in which the tillering of the plant cultivated by using the tillering promoter of the present invention are superior to the tillering of the plant cultivated under entirely the same conditions with the exception that the tillering promoter of the present invention is not applied. It is possible to determine the amounts by some preliminary comparative test which is easy to carry out for those skilled in the art. For example, in the case of foliar application in a liquid form (as an agent for foliar application), proline may be applied at a low concentration, e.g., as low as 0.2 ppm within the above concentration range. That is, the tillering promotion of lawn grass is effected at such a low concentration. In addition, the application amounts of inosine may be in a range of 0.05 to 1 ppm to soil (5 to 100 g per 100 tons of soil), and in the case of hydroponic cultivation, inosine may be applied in an amount of 0.1 to 2 ppm to hydroponic medium.

By the way, the tillering promoter for a plant of the present invention may be in a form containing also (mixing) inosine in addition to a predetermined amino acid as explained in the above. However, the amino acid and inosine may be, of course, applied each at the same time or at slightly different times. Such an application way is also an embodiment of the present invention. As a formulation suitable for such an application way, there may be mentioned a kit form wherein the amino acid and inosine are packaged separately and both the packages are made one set.

EXAMPLES

In the following will be explained the present invention in further detail with reference to the Examples.

Example 1

Effect of Proline on Hydroponic Cultivation of Lawn Grass (1)

Seedlings of grass (a European grass; bent grass) were raised and divided into four groups of A to D, and hydroponic cultivation was carried out (Table 1 shown below). Concerning Groups B and D, inosine was added to each hydroponic medium in such amount that the concentration became 2 ppm. Concerning Groups C and D, proline was applied onto leaf surfaces once a week in an amount of 20 ppm. Group A was the control. Upon confirmation on the 40th day, the tillering promotion was clearly observed in the two groups of C and D wherein proline had been applied onto leaf surfaces, but no tillering promotion was observed in Groups A and B which had not been applied. Furthermore, five average stocks which had not been withered were sampled from each group and examined. As shown in the following Table 1, with regard to all of the root length, leaf length and number (above-ground parts), total weight of the living plant, and tillering number, good growth was found in the proline-treated plots. Especially, it was confirmed that the effect became more remarkable when inosine was used in combination.

TABLE 1

Comparison of the lawn grasses between the groups (5 roots each)

| | Average root length (cm) | Average leaf length (cm) | Number of leaves per one root | Total weight of living plants per five roots (g) | Number of tillering per one root |
|---|---|---|---|---|---|
| A (Control) | 1 | 18 | 5 | 0.28 | 1 |
| B (Inosine) | 2 | 20 | 7 | 0.40 | 2 |
| C (Proline) | 1 | 22 | 16 | 0.53 | 5 |
| D (Inosine + Proline) | 3 | 22 | 23 | 1.00 | 6 |

Example 2

Effects of Proline, Glutamine, Arginine and Urea on Hydroponic Cultivation of Grass Seedlings of grass (a European grass: bent grass) were raised and divided into five groups of A to E, and hydroponic cultivation was carried out (Table 2 shown below). Group A was the control. Concerning Group B, proline was applied onto leaf surfaces once a week in an amount of 20 ppm. And, concerning the three groups of C to E, aqueous solutions of arginine, glutamine, and urea were applied onto leaf surfaces, respectively, once a week in such a amount that the nitrogen amount was the same as that of the proline in Group B. Upon confirmation on the 40th day, the tillering promotion was clearly observed in the groups of B to D, but no tillering promotion was observed in the groups of A and E.

Furthermore, five average stocks which had not been withered were sampled from each group and examined. As shown in the following Table 2, with regard to the number of leaves and total weight of the living plant, good results were observed in the plots treated with proline, glutamine, and arginine, and the effects were more remarkable than that of urea which is a generally-used nitrogen source for foliar application.

TABLE 2

Comparison of the lawn grasses between the groups (5 roots each)

|  | Average root length (cm) | Average leaf length (cm) | Number of leaves per one root | Total weight of living plants per five roots (g) | Number of tillering per one root |
|---|---|---|---|---|---|
| A (Control) | 2 | 14 | 8 | 0.33 | 2 |
| B (Proline) | 2 | 14 | 17 | 0.60 | 5 |
| C (Arginine) | 2 | 18 | 9 | 0.51 | 3 |
| D (Glutamine) | 2 | 18 | 11 | 0.66 | 3 |
| E (Urea) | 2 | 15 | 6 | 0.34 | 1 |

Example 3

Effect of Proline on Hydroponic Cultivation of Grass (2)

Seedlings of grass (a European grass: bent grass) were raised and divided into six groups of A to F, and hydroponic cultivation was carried out (Table 3 shown below). At that time, inosine was added to the hydroponic media for all the groups in such amount that the concentration became 2 ppm in each hydroponic medium. Group A was the control. In the groups of B to F, proline was applied onto leaf surfaces once a week with the concentration being changed stepwise. Upon confirmation on the 40th day, the tillering promotion was clearly observed in the groups of B to F, but no tillering promotion was observed in Group A. However, inhibition of the growth or withering was observed in Group F.

Furthermore, five average stocks which had not been withered were sampled from each group and examined. As shown in the following Table 3, with regard to the number of leaves and total weight of the living plant, good results were observed in the plots treated with proline at a concentration of 2 ppm to 0.2%.

TABLE 3

Comparison of the lawn grasses between the groups (5 roots each)

|  | Average root length (cm) | Average leaf length (cm) | Number of leaves per one root | Total weight of living plants per five roots (g) | Number of tillering per one root |
|---|---|---|---|---|---|
| A (Control) | 3 | 22 | 14 | 0.59 | 2 |
| B (2 ppm Inosine) | 4 | 24 | 14 | 1.04 | 3 |
| C (20 ppm Proline) | 4 | 24 | 15 | 0.95 | 4 |
| D (200 ppm Proline) | 5 | 24 | 24 | 1.01 | 4 |
| E (0.2% Proline) | 5 | 23 | 14 | 0.90 | 3 |
| F (2.0% Proline) | 3 | 19 | 11 | 0.40 | 3 |

[Effects of the Invention]

According to the present invention, the application of at least one of proline, arginine and glutamine, or the application of inosine in addition to the amino acid(s) promotes the tillering of a plant, especially lawn grass, and also affords a nutrition effect easily.

What is claimed is:

1. A method for tillering promotion of lawn grass, comprising:

applying at least one amino acid selected from the group consisting of arginine, glutamine and proline onto the surfaces of the leaves of lawn grass; and applying inosine to the subterranean part(s) of the lawn grass.

2. The method according to claim 1, wherein said amino acid is applied to the leaves of grass in a concentration of from 0.2 ppm to 0.2%.

3. The method according to claim 2, wherein said concentration of said amino acid ranges from 10 to 300 ppm.

4. The method according to claim 3, wherein said concentration of said amino acid ranges from 100 to 300 ppm.

5. The method according to claim 1, wherein said inosine is applied to the soil in an amount of from 5 to 100 g per 100 tons of soil.

6. The method according to claim 1, wherein said at least one amino acid has been purified to a purity of 90% or more.

7. The method according to claim 1, wherein said at least one amino acid has been dissolved in a solvent.

8. The method according to claim 1, wherein said at least one amino acid has been formulated into a powder, granule or tablet.

9. The method according to claim 1, wherein arginine is applied onto the surfaces of the leaves of lawn grass.

10. The method according to claim 1, wherein glutamine is applied onto the surfaces of the leaves of lawn grass.

11. The method according to claim 1, wherein proline is applied onto the surfaces of the leaves of lawn grass.

* * * * *